US006405934B1

(12) United States Patent
Hess et al.

(10) Patent No.: US 6,405,934 B1
(45) Date of Patent: Jun. 18, 2002

(54) OPTIMIZED LIQUID DROPLET SPRAY DEVICE FOR AN INHALER SUITABLE FOR RESPIRATORY THERAPIES

(75) Inventors: Joseph Hess, Vignes Perdues; Hu Bo, Peseux; Raphael Weber, La Chaux-de-Fonds; Isabel Ortega, Ruedes Jeanneret; Cedric Barraud, Haulerive; Nicolaas Frans de Rooij, Bôle; Bas de Heij, Neuchatel, all of (CH)

(73) Assignee: Microflow Engineering SA, Neuchatel (CH)

( * ) Notice: Subject to any disclaimer, the term of this patent is extended or adjusted under 35 U.S.C. 154(b) by 0 days.

(21) Appl. No.: 09/442,270

(22) Filed: Nov. 17, 1999

(30) Foreign Application Priority Data

Dec. 1, 1998 (EP) .......................................... 98122751
Apr. 15, 1999 (EP) .......................................... 99107553

(51) Int. Cl.[7] .............................................. B05B 17/04

(52) U.S. Cl. .................. 239/4; 239/102.2; 128/200.16; 128/200.14

(58) Field of Search .......................... 239/102.2, 102.1, 239/4; 346/140.1, 141; 347/6, 9, 20, 47, 68, 70; 128/200.16, 200.14, 204.23; 264/9

(56) References Cited

U.S. PATENT DOCUMENTS

| | | | | | |
|---|---|---|---|---|---|
| 3,960,324 | A | * | 6/1976 | Titus et al. | 239/102.2 |
| 4,530,464 | A | | 7/1985 | Yamamoto | |
| 4,558,333 | A | * | 12/1985 | Sugitani et al. | 346/140.1 |
| 4,605,167 | A | | 8/1986 | Maehara | |
| 4,659,014 | A | * | 4/1987 | Soth et al. | 239/102.2 |
| 4,667,877 | A | * | 5/1987 | Yao et al. | 239/102.2 |
| 4,719,480 | A | * | 1/1988 | Elrod et al. | 239/102.2 |
| 4,871,489 | A | * | 10/1989 | Ketcham | 264/9 |
| 5,487,378 | A | * | 1/1996 | Robertson et al. | 128/200.16 |
| 5,497,763 | A | | 3/1996 | Lloyd et al. | |
| 5,725,153 | A | * | 3/1998 | Wang et al. | 239/102.2 |
| 5,828,394 | A | | 10/1998 | Levin et al. | |
| 6,196,219 | B1 | * | 3/2001 | Hess et al. | 128/200.21 |

FOREIGN PATENT DOCUMENTS

| | | | | |
|---|---|---|---|---|
| DE | 264552 | * | 2/1989 | 239/102.2 |
| EP | 0 516 565 | | 4/1996 | |
| EP | 0 641 934 | | 12/1996 | |
| EP | 0 824 023 | | 2/1998 | |
| EP | 0 923 957 | | 6/1999 | |
| WO | 90/01997 | | 3/1990 | |
| WO | WO 92 11050 | | 7/1992 | |
| WO | 95/15822 | | 6/1995 | |
| WO | WO 95 25601 | | 9/1995 | |

OTHER PUBLICATIONS

Pharmaceutical Development and Technology, 1(3), 261–268 (1996), Abstract for "Comparison of a Respiratory Suspension Aerosolized by an Air–Jet and an Ultrasonic Nebulizer", Susan L. Tiano et al.

* cited by examiner

*Primary Examiner*—Henry C. Yuen
*Assistant Examiner*—Dinh Q. Nguyen
(74) *Attorney, Agent, or Firm*—Griffin & Szipl, P.C.

(57) ABSTRACT

The liquid droplet spray device (1) comprises a housing formed of a superposition of a first and a second substrate (5, 6) and a space (2) within the housing for containing a liquid substance (3), vibrating means (8) for applying a frequency vibration to the substance (3) thereby generating the liquid droplet spray, and outlet means (7, 9, 10) for ejecting the liquid droplet spray. The outlet means comprise a cavity (7), output nozzles (9) and output channels (10) connecting the cavity (7) to the outlet nozzles (9). According to the invention, the vibrating means (8) creates a standing wave pattern within the liquid substance (3), and the outlet means are arranged such that said outlet nozzles (9) are superposed on the vibration mode peaks of the standing wave pattern. Advantageously, the first and second substrates have similar geometrical shapes. Minimal retention and optimal flow of the substance are obtained.

29 Claims, 4 Drawing Sheets

OPTIMIZED LIQUID DROPLET SPRAY DEVICE FOR AN INHALER SUITABLE FOR RESPIRATORY THERAPIES

BACKGROUND OF THE INVENTION

This application claims priority of European patent application 122 751.5 filed Dec. 1, 1998 and European patent application 107 553.2 filed Apr. 15, 1999. The entire disclosure of the above patent applications is incorporated by reference herein.

The present invention relates generally to drug administration devices, and in particular to a liquid droplet spray device for atomizing a liquid substance such as a drug, a fragrance or other aerosolised or atomized liquids. Such a device may be used for administrating a drug to a patient by means of his or her respiratory system. Such an administration device, in its simplest form, is commonly called an inhaler. It may be used, e.g., for the controlled administration of drugs or for a variety of therapies using aerosolised drug administration including anesthetics. The inhaler delivers the drug, which is in the form of a liquid substance, as a dispersion of atomized droplets. More specifically, the present invention concerns an optimized liquid droplet spray device which efficiently creates and which fully expels a liquid droplet spray.

Various devices are known for atomizing a liquid. Document EP 0 516 565 describes am ultrasonic wave nebuliser which atomizes water. This apparatus is used as a room humidifier. Vibration is transmitted through the water to the water surface from which the spray is produced. A perforate membrane is provided to retain the water in absence of oscillation.

Typically, inhaler devices use the same principle to atomize the liquid into droplets, see for example the document WO 95/15822. However, such devices are particularly ineffective in vaporizing suspensions as explained in the Research Article <<Comparison of a respiratory suspension aerosolised by an air-jet and an ultrasonic nebuliser>> by Susan L. Tiano and Richard N. Dalby in Pharmaceutical Development and Technology, |(3), 261–268 (1996).

Furthermore, the droplet size which depends on the size of the outlet orifices of the perforate membrane, further also depends on the shape of the orifice and on the vibration frequency. In order to obtain a small droplet, a very high frequency should be used, typically over 1 MHz for droplets of about 10 $\mu$m in diameter. This leads to an increased power consumption due to the high frequency so that such a device is not suitable for a small battery operated device.

With a large variation of droplet size, it is almost impossible to determine the expelled quantity and thus the actually-administered dosage.

Further, the orifices can not be made too small, not only because of fabrication reasons, but also in order to avoid clogging of the outlet orifices by the substance. In fact, it is known that the aqueous solubility of the substance solution depends on the composition of the drugs used and on its temperature. It is also known that such orifices might be clogged by very small amounts of drug left in the liquid spray device after atomization.

To ensure that a certain amount of substance is indeed released, it has been proposed to monitor the amount of liquid released when the inhaler is used. The document WO 92/11050 describes such an inhaler having means for cyclically pressurizing the liquid such that the liquid is periodically expelled and also having control means for deactivating the droplet generator after a predetermined time, e.g., by using a timer, or, after a predetermined volume of liquid has been expelled. However, this document is completely silent about droplet size control, aqueous solution or suspension characteristics as well as about any deposition target determination and control of the liquid.

Another prior art device is known from the document U.S. Pat. No. 5,497,763. This device has a breath actuated release of aerosolised drug and has a porous membrane located above a dosage unit container. The pores are preferably cone-shaped to reduce the force needed to move the drug substance there through when collapsing the container. However, such a membrane is difficult to manufacture, as the reproducibility of the pores is poor. Also, the difference in length and diameter of the pore channel results in a considerable difference of pressure drop across this channel. This varying pressure drop will thus also lead to a variation of the quantity and droplet size dispersion of the drug being expelled. Another problem is the alignment of the movable membrane with pores over each unit container resulting in another source of uncertainty over the expelled amount of drug.

The pre-cited documents are silent about avoiding layers or areas of liquid drug forming on the outside surface of the nozzle array by well-known capillary action and stiction. This is especially the case with devices where the same nozzle array is used several times, such as for example in the documents WO 92/11050 or WO 90/01997. Such layers lead to the forming of liquid meniscus in front of the nozzles which are broken up by the piezo-activated spraying action but lead to a larger droplet size dispersion than without such layers.

Although the cited document U.S. Pat. No. 5,497,763 partially overcomes this problem by separating dosage containers and the porous membrane through which the drug is aerosolised, this solution does not allow for the precision and repeatability of the cone-shaped pores used and the precise control of the drug delivery, requiring a pressure to be applied additionally to the piezoelectric vibrating means to force the liquid out. Also, the pre-cited documents do not mention that the piezoelectric vibrating means is not compensated for its non-linearities adding to uncontrolled factors affecting the delivery of targeted delivery.

The document U.S. Pat. No. 4,605,167 also describes a liquid droplet spray device for use in a fuel injector or an ink jet printer. The spray device comprises a housing provided with a liquid containing space and having a top substrate forming a membrane and provided with outlet nozzles therein. A piezoelectric actuator is attached to the membrane to vibrate the latter thereby causing the ejection of the liquid which is sucked out of the space by the vibrating membrane. Thus, when the membrane deflects inwardly towards the liquid, it compresses the latter and by expanding again, the created pressure in the liquid ensures the droplet ejection, i.e. the liquid is sucked towards the membrane and is expelled through the outlet nozzle. Another prior art document which basically functions according to the same principle is known from U.S. Pat. No. 5,828,394.

However, such spray devices suffer from the inability to fully empty the liquid in the space. Indeed, if the liquid is a suspension containing solid particles, these particles will not be sucked towards the membrane because they are too heavy. Thus, a precise dosing is not possible, because the retention cannot be determined. Furthermore, the pressure created in the liquid by the incoming membrane causes another problem related to the ejected droplet. Indeed, a droplet that is ejected through the outlet nozzle usually has a pear-shape, with the large body part tearing apart at the exit, and a smaller cut-off tail part thus being ejected slightly later. However, due to the pressure of the liquid, the tail part will regain the body part, and the total large droplet impacts simultaneously the target. It may be thus understood that an exact determination of the expelled amount of liquid and an exact control of the droplet size are impossible.

SUMMARY OF THE INVENTION

It is, therefore, an object of the present invention to provide an improved liquid droplet spray device for an inhaler suitable for respiratory therapies which overcomes, at least partially, the inconveniences of the prior art and which allows for an optimal flow of the atomized substance and which allows for a minimal retention of the substance in the spray device after expelling so that a precisely determined quantity may be expelled.

It is another object of the present invention to provide such a device which is simple, reliable to manufacture, small in size and low in cost.

Thus, the present invention concerns a liquid droplet spray device as disclosed and described herein.

Thanks to the specific shape and the positioning of the outlet means of the spray device according to the present invention an optimal throughput and flow together with a minimal retention of the atomized liquid in the spray device is obtained so that a precise dosage of expelled liquid may be determined.

Further, the inventive spray device may be re-used for a certain number of doses, because, due to the minimal retention, there is a minimal risk of increased drug concentration or drug contamination with remains of the previously used liquid.

Further, thanks to the inventive spray device, only a minimal amount of liquid is used, as the exact amount released can be predetermined with a high precision so that there is only a very small amount of waste and that the side effects can be limited too.

BRIEF DESCRIPTION OF THE DRAWINGS

Other features and advantages of the liquid spray device according to the present invention will become clear from reading the following description which is given solely by way of a non-limitative example thereby referring to the attached drawings in which.

BRIEF DESCRIPTION OF THE PREFERRED EMBODIMENTS

Figure 1:
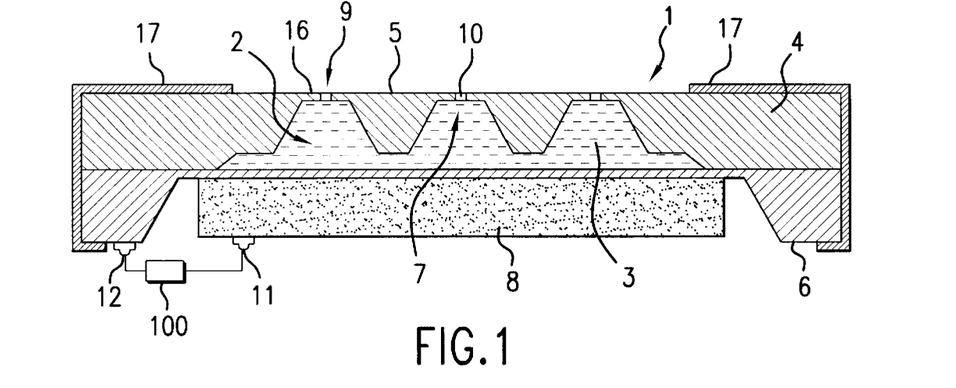
FIG. 1 is a schematic cross-section of a first preferred embodiment of the liquid droplet spray device according to the present invention.

Referring now to FIG. 1, a first embodiment of a liquid droplet spray device for an inhaler suitable for respiratory therapies is indicated by general reference 1. A suitable inhaler and other embodiments are described in more detail in the document EP 0 824 023 and in co-pending European patent application no. 98111497.8 which is incorporated herein by reference.

Spray device 1 consists of a housing formed of a superposition of a first, or a top substrate 5 and a second, or a bottom substrate 6 in-between which a chamber or a space 2 is formed for containing a liquid substance 3. Top substrate 5 contains outlet means consisting of cavities 7 which partly constitute space 2, outlet nozzles 9 and outlet channels 10 connecting these nozzles to the cavities 7.

Liquid substance 3 enters spray device 1 by way of, e.g., a very low pressure, e.g., around a few millibar, or capillary action. Such very low input pressure is preferably at a constant and repeatable value and is important to provide very low exit velocity of the aerosol which is consequently easily absorbed into the inhalation air stream, limiting medication deposition losses in the extrathoracic region. This can be achieved for example by way of at least one input tube or needle 4 through which a liquid substance may be supplied, directly or via a valve, from an external reservoir (not shown), which may be included in the inhaler, into spray device 1. In the example shown, this input tube 4 is located at a side of the spray device 1, but this input needle may of course also be located elsewhere, e.g., below the spray device and traversing its housing or traversing further provided vibrating means 8 and bottom substrate 6 to reach space 2. The filling of space 2 may also be piston or plunger activated, however with pressure reduction or performed by way of valves or a pump or a micropump at very low pressure. This may be carried out as described in the document EP-A-0 641 934. Thus space 2 is dimensioned such that it may contain the required amount corresponding to the desired unit dose and can include corresponding dosage valves.

Figure 2A:
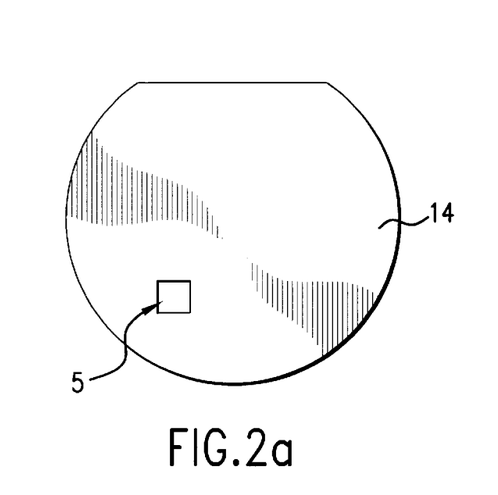
FIG. 2 is a schematic view of a wafer and mask which may be used to manufacture the liquid droplet spray device according to the present invention.
Figure 2B:
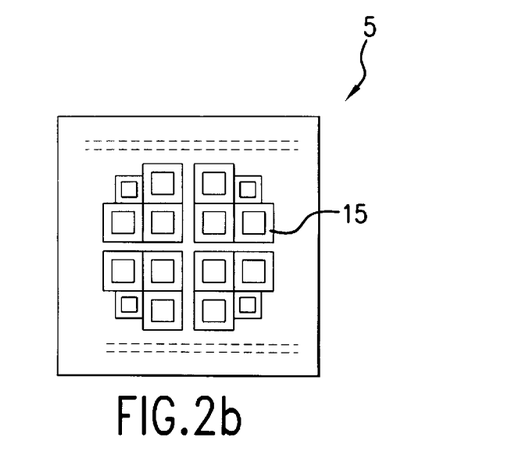

Referring now to FIG. 2, both substrates are manufactured in a similar manner e.g. by etching a silicon wafer 14 in a suitable manner by using a mask in a manner well known to a skilled person to obtain a plurality of substrates, in this example top substrates 5, per wafer. The FIG. 2b shows a part of a mask corresponding to that required to obtain top substrate 5. The distribution and shape of the cavities shown here can take on many different forms. The arrangement resulting from a mask 15 according to FIG. 2b is just one example. Space 2 is thus obtained by partially etching top substrate 5 and bottom substrate 6. However, it is also possible to etch only top substrate 5 depending on the final arrangement of these two substrates relative to each other for enclosing space 2. In the preferred embodiment, bottom substrate 6 is also etched so as to form a thinner middle section which may act as a membrane for transmitting a vibration. This bottom substrate may be arranged such that its etched surface is facing the etched surface of top substrate 5 thus obtaining a large space 2. In the embodiment as shown in FIG. 1, however, bottom substrate 6 is arranged upside down such that its flat surface faces the etched surface of top substrate 5. In this manner, the bottom exterior part of the housing formed by these substrates has a thinner middle section into which vibrating means 8 may be placed so as to obtain a compact device as will be explained further on.

Bottom substrate 6 may be made of glass, ceramics, silicon, high-density polymer or the like. Top substrate 5 preferably consists of silicon, but it may consist of plastic, high density polymer, ceramics, metal or silicon or the like for its main body, and of silicon for its nozzle body as will 
be explained in more detail further on. The substrates 5 and 6 are attached to each other, preferably by anodic bonding, so as to form and enclose space 2. As mentioned, the present example shows a preferred embodiment in which bottom substrate 6 is fitted so that the bottom of space 2 is flat, this allowing for a high compression of the volume of space 2 and for a compact spray device 1.

A selective hydrophilic coating, e.g., an amorphous material such as $SiO_2$ or sputtered glass or Pyrex™, may further be applied to provide a protective layer around the inside walls of space 2 and/or of cavities 7 to avoid any contamination of substance 3 by the material of these walls and to improve wettability in certain parts. This may be carried out as described in the document EP-A-0 641934. This hydrophilic coating which may be applied as a selective, patterned coating is advantageously coupled with a selective, patterned hydrophobic coating in certain areas of space 2, cavities 7 and on the outside of top substrate 5. In order to maintain the protective aspect of these surfaces and at the same time to reduce the internal and external stiction due to capillary forces in space 2, and especially on the outside of top substrate 5, a hard amorphous carbon film, e.g. a diamond-like carbon (DLC), is provided, preferably in a selective patterned manner in these areas. Such selective film coating also allows for a more complete emptying of space 2 due to reduced stiction resulting in a minimal retention of the used liquid substance. Such coating and its hydrophobic properties can be enhanced by fluorine plasma.

The present Applicant has found that such surface property specific DLC coating influences and improves droplet size dispersion, provides an even better mono-dispersive pattern released by the spray device and prevents extractables or leachable components and bio-contamination.

Figure 3A:
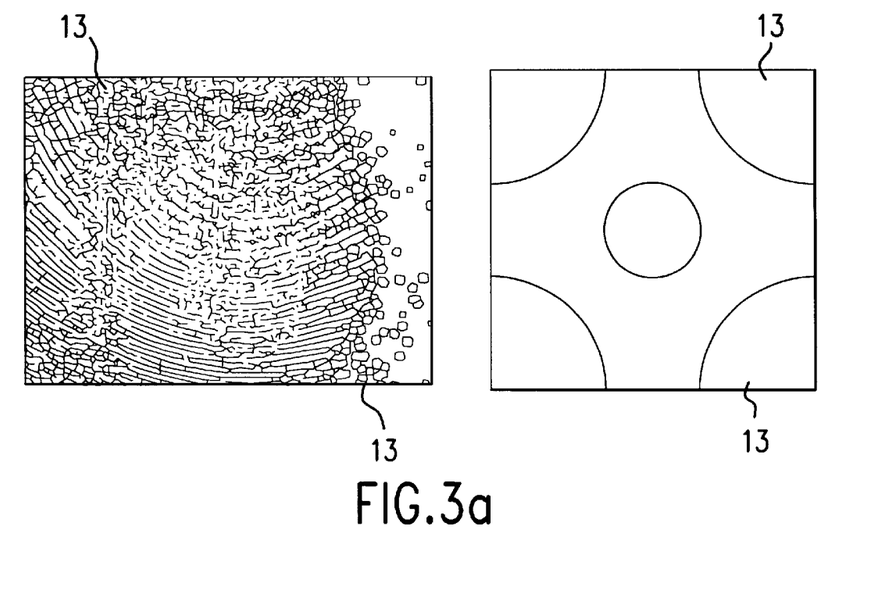
FIG. 3 is a schematic top view of the vibration modes in the vibrated liquid substance of the liquid droplet spray device according to the present invention.
Figure 3B:
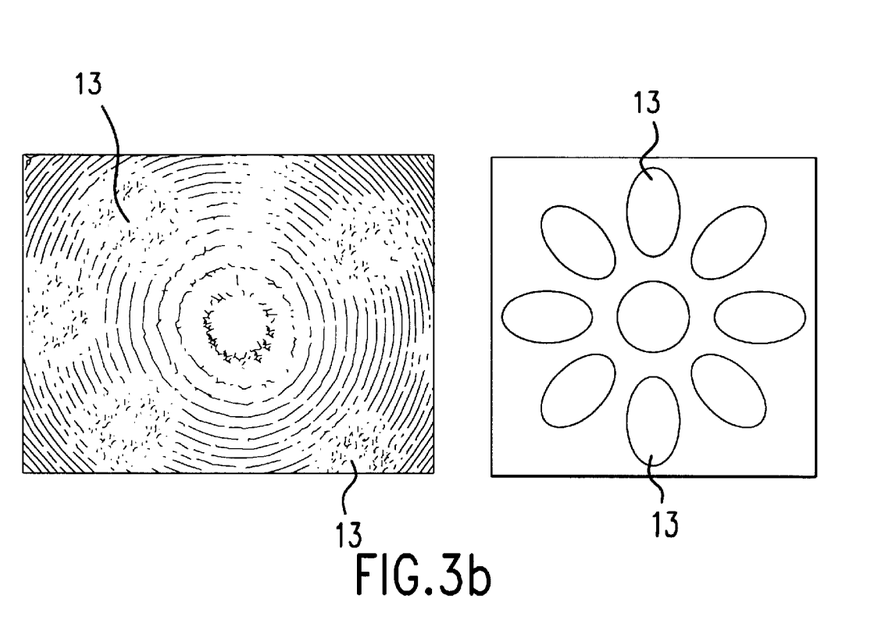

Of course, the hydrophobicity and the hydrophilicity of top substrate 5 and bottom substrate 6 may be inverted if so required by the flow characteristics of the medication or liquid substance 3.

If top substrate 5 is made, at least partially, of a polymer, then a polymer with very low surface energy is used advantageously in combination with the selectively patterned hydrophobic coating. If this substrate 5 is made of a polymer, acrylic or e.g. a photosensitive epoxy including or not said selective hydrophobic coating, e.g. a diamond-like nano-composite or Teflon® coating, a silicon etched mask, using the deep silicon etching process described hereafter, is preferably used by providing the masks on the wafer used to obtain the top substrate to facilitate precise plasma etching, e.g. O2 plasma or UV exposure of photosensitive materials, of the channels and of the output nozzles which are provided in the top substrate in said materials, as will be explained in more detail further on.

Spray device 1 preferably comprises a vibrating element 8, e.g., a piezoelectric element, attached to the exterior bottom surface of bottom substrate 6 in the vicinity of its thinner middle section to cause vibration of substance 3 in space 2 through the membrane part of second, or bottom substrate 6. However, this element may also be located separated from spray device 1 directly onto a Printed Circuit Board (PCB). This element may be glued to or deposited on the bottom surface of the spray device or on the PCB. Electrodes 11 and 12 are applied to piezoelectric element 8 and to bottom substrate 6 respectively. These electrodes may be spring-contacts which contact appropriate electrodes (not shown) connected to electronic control means which may be included in the inhaler itself. If the element is arranged on the PCB with or without intermediary elements, clamping means may be provided to bring the spray device into contact with the piezoelectric element 8. As already mentioned, by assembling this piezoelectric element to the thinner middle section of the bottom substrate 6, a very compact spray device may be obtained.

Advantageously, vibrating means 8 is operably connected to electronic device or means 100, for detecting a particular vibration mode of the piezoelectric element, for maintaining that particular mode and for compensating for any non-linear effects due to a change in ambient conditions of the place of use of spray device 1.

It has been observed that the droplet size is inversely proportional to the excitation frequency as of a particular frequency and pressure. Preferably, piezoelectric element 8 vibrates at that particular frequency which may be for example around 243 kHz. Of course other frequencies may be used if appropriate. Indeed, several embodiments have been satisfactorily tested by the Applicant at a frequency of 100 kHz and even of 30 kHz. It should be noted that the lower the frequency, the lower the power consumption, but the higher the number of outlet nozzles so as to obtain a desired liquid substance output. This vibration may be generated in a known manner e.g. by using a frequency oscillator.

According to the present invention, the Applicant has noticed that when vibrating bottom substrate 6 at certain frequencies, a standing wave pattern is created in space 2, which thus traverses the liquid substance. For a specific frequency, vibration mode peaks are generated at specific places. These vibration modes provoke a vibration of top substrate 5 containing the outlet nozzles 9. This top substrate may be considered a membrane. Indeed, the vibration of the liquid substance is transmitted to the membrane and causes a pressure increase due to the compression of the vibrating means 8 and space 2 thus causing the atomization of the liquid substance. At certain places where outlet channels 10 and outlet nozzles 9 are located, the membrane has a thickness which is thin enough, in the present example around 20 $\mu$m, to allow a vibration of this membrane, or this top substrate 5 as a function of the applied frequency. This vibration frequency of the top substrate 5 may be higher than the applied frequency. This effect is probably due to addition of frequencies. When creating the outlet means comprising the channels 10 and nozzles 9, care should be taken to arrange these outlet means such that they are substantially superposed on the vibration mode peaks of the standing wave pattern created in space 2 containing the liquid substance. In such a case, an optimized flow and throughput of the atomized liquid substance through the channels and nozzles is obtained thus resulting in a minimal retention of the liquid substance in space 2 and a very precise determination of the expelled amount of liquid substance.

The corresponding vibration mode can also be selected to invert the flow. Applicant has observed for example that a liquid droplet spray device 1 whose expelling vibration frequency and mode peaks occur around 270 kHz, was drawing tiny liquid droplets on the outer surface of top substrate 5 through the nozzles 9 and channels 10 back into device 1 and back past the entry channel 4 under certain conditions e.g. at a frequency around 70 kHz featuring emptying internal space 2 after inhalation. Electronic means, not represented, can be used advantageously to select, control and maintain the desired vibration mode for minimum retention and to compensate for any non-linear effects as mentioned earlier.

FIGS. 3*a* and 3*b* show the vibration mode peaks 13 created in the liquid and on the membrane part of the top substrate 5 for two different frequencies, in FIG. 3a the applied frequency being around 139.9 kHz, and in FIG. 3b around 243 kHz. From this it is clear that by correctly positioning the outlet nozzles 9 with respect to the mode peaks, an optimized liquid droplet spray device may be obtained which has a maximal flow and a minimal retention of liquid substance 3.

Figure 4:
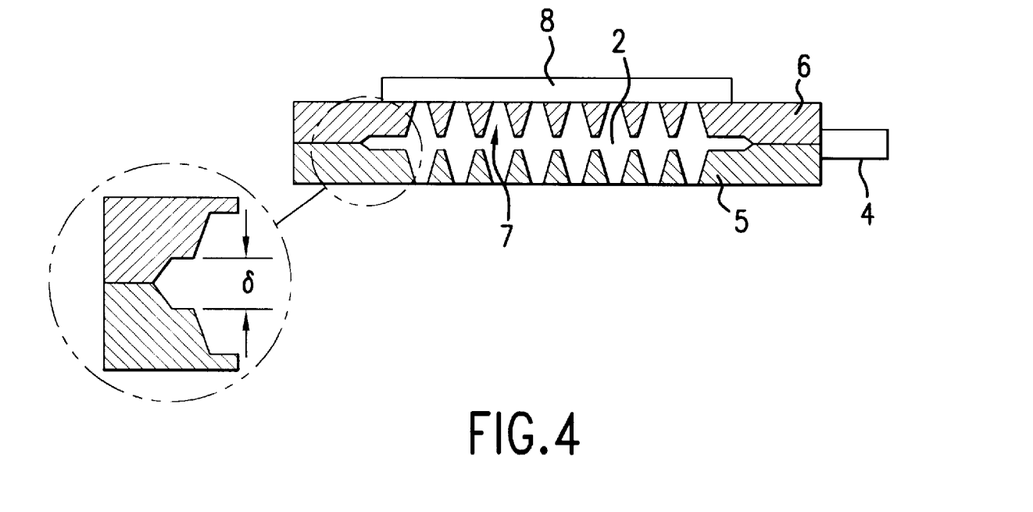
FIG. 4 is a schematic cross-section of a second preferred embodiment of the liquid droplet spray device according to the present invention.

FIG. 4 shows a second preferred embodiment of the liquid droplet spray device according to the present invention. This spray device is similar to that of the first embodiment shown in FIG. 1 except for the fact that the first or top substrate 5 and the second or bottom substrate 6 are in this case identical. The same reference signs are used for similar components. In this example, bottom substrate 6 has a shape very similar to that of top substrate 5 comprising the outlet means. As can be seen, bottom substrate 6 also has cut-off pyramid-shaped cavities 7 in a similar manner as the top substrate. Output channels 10 may also be provided in this bottom substrate. Of course, no output nozzles 9 are provided in the bottom substrate, but its general geometrical shape resembles that of top substrate 5. By thus constructing the spray device, space 2 is created having a specific shape due to the fact that both substrates are provided with the cut-off pyramid shaped cavities. Space 2 has a chamber depth, designated by reference sign δ, which is defined as shown in FIG. 4 as being the distance between the two inner surfaces of the substrates before the micro-machining of the cavities has been carried out.

As is generally known, objects that are geometrically and material-wise the same will have the same resonance frequency. Thus, by providing two similar substrate structures as the top and bottom substrates, the only anti-symmetry left is the vibrating means 8 which is arranged on the outside of bottom substrate 6. This design gave even better results than the first embodiment due to the fact that the first modal frequencies within space 2 originating from the inner surface of the bottom and the top substrate only differ by a factor 1.2. Anti-symmetrically changing the chamber depth δ can bring the two modes further together. However, even when these first modes do not appear together there still are some interesting modes at higher frequencies. In such a case, a mode on one side can induce a similar vibration on the other side. In practice, this embodiment was found to be more stable.

As already mentioned, the outlet means should be placed there where there is sufficient amplitude for droplet ejection, hence close to the peaks or extremes of the mode, because with enough kinetic energy, the liquid breaks off the nozzle and forms a small droplet. Nozzles that are not properly placed can cause large droplets on the front outer surface of top substrate 5, which in turn can block other output nozzles.

Advantageously, a flexible heating surface, such as a captan film with heating element 17, see FIG. 1, can be suitably fitted on substrates 5 and 6, to heat the liquid substance, to e.g. around 37° C., by applying an electric current in an appropriate manner to this heating element. Of course, it is also possible to deposit a conductive material on the inner surface of bottom substrate 6, which thus corresponds to the bottom of space 2, to heat the liquid by applying a current to this conductive material.

The present Applicant has also detected that such heating effect can be generated advantageously by operating vibrating means 8 at a particular vibration frequency and mode at which there is no ejection of the liquid substance, but there is a heating effect caused by the vibrating means 8, e.g. at 70 kHz but also at other frequencies. In this case vibrating means 8 renders a separate heating element such as heating element 17 superfluous, as the vibrating means itself may thus act as a heating element.

Thanks to such heating, the influence of any temperature fluctuations on substance 3, and in particular on the particles which this substance contains, may be largely controlled. In fact, it is known that the dimensions of steroids which are commonly used in a drug substance vary with the temperature and become more soluble with a higher temperature, see for more details the article "Steroid/Cyclodextrin complexes for pulmonary delivery" by G. M. Worth, M. Thomas, S. J. Farr and G. Taylor; Proceed. Int'l Symp. Control. Rel. Bioact. Mater., 24 (1997), pages 747 & 748, Controlled Release Society Inc. Furthermore, thanks to this heating, humidity influences due to the environment in which the spray device operates may also be taken into account to ensure correct functioning.

Furthermore, such heating may contribute before or at the beginning of the atomization cycle to operate the liquid droplet spray device 1 under defined ambient and operating conditions.

Also, such heating may further contribute at the end of the atomization cycle to evaporate any minute amount of liquid present in space 2, same as a continuation for a predetermined time of the actuating of the vibrating means after the inhalation cycle has ended thereby obtaining the aforementioned inverted flow.

Furthermore, this heating is of course advantageous for dispersing the liquid droplet spray under extreme ambient conditions, e.g. at a temperature of less than −10° C. This heating can also be extended to the aforementioned external reservoir and valve supplying the liquid substance to inner space 2.

An example of the dimensions of the different parts of spray device 1 is given hereafter. The vibrating means 8 is around 300 μm thick. The thinner middle section of bottom substrate 6 is around 50 μm, whereas the bottom substrate and the top substrate 5 are both around 400 μm (i.e. the wafer thickness) for a spray device having a total top surface of about several square millimeter.

In a preferred embodiment, top substrate 5 is formed of silicon as it may be micro-machined to obtain a very high precision manufacturing, such a high precision and absence of leachable components being much more difficult to obtain with plastics or the like, for instance by using UV exposure or a plasma etching treatment of various plastic material, but silicon is also more expensive than plastics. As mentioned, outlet nozzles 9 and accesses or outlet channels 10 are formed in top substrate 5, so that the excited substance 3 may leave device 1 as a droplet spray. To this effect, this top substrate 5 is micro-machined, for example in a well known anisotropic etching manner at several places, by using an appropriate mask 15 as shown in FIG. 2, to obtain tapered, cut-off pyramid-shaped cavities 7 which are, for example, about 200 to 400 μm deep. These cut-off pyramid-shaped cavities can have a square or an elongated base and be of any number to provide the correct internal volume and flow characteristics for a particular substance 3. However, the specific shape of these cavities is not important, but mainly depends on the method of manufacturing them. By using the usual micro-machining techniques, anisotropic etching is used, thus resulting in the tapered cut-off pyramid shape, but the cavities may also be straight or cylindrical or of another suitable geometrical shape.

Each cavity 7 then has a flat top surface having a side length of about 200–400 μm. Within this top surface of each cavity 7 at least one output channel 10 is provided to connect cavity 7 to an outlet nozzle 9 at the exterior of top substrate 5. This output channel is preferably micro-machined using a deep reactive vertical plasma etching of silicon, e.g. at room temperature or low temperature, and an advanced silicon etch solution process. The present Applicant has realized multi-cavity designs where each flat top surface is up to 800×800 $\mu$m and contains more than 100 output channels. The Applicant has developed techniques to machine these channels with a vertical and smooth profile, thereby significantly reducing undercutting and maintaining tight control over tolerances. This provides for a precisely defined pressure drop, droplet size and flow behaviour across channel 10 for aqueous solutions and suspensions whereas the smooth surface is suited for medications carrying small solid particles, e.g. from less than 1 to 3 $\mu$m, in suspensions. The same effect can be obtained proportionally with larger dimensions, e.g. with nozzles of 10 $\mu$m or larger for example for nasal applications.

Thus, at the outer end of each output channel 10 at least one output nozzle 9 is provided through which the excited liquid substance is ejected as a droplet spray. The used technology allows to etch extremely precise, deep channels having straight and smooth side-walls and being round or square with a very tight, repeatable tolerance and allows to etch areas around nozzles 9 as explained here below. The process between lithography and etching can be arranged so as to adapt the lithography mask to the desired diameter as a function of the process tolerances thus guaranteeing the uniform precision of the nozzles and of the droplets. In the present example, each output channel 10 is about 20 $\mu$m long and 5 $\mu$m wide with nozzle 9 having a maximum opening of around 5 $\mu$m. Dimensions as well as the number of nozzles may of course be readily modified depending on the amount of drug and on the corresponding droplet size to be ejected as will be explained in more detail hereafter. However, it should be noted that the length of this output channel 10 should not be too long to avoid a large pressure drop across this channel resulting in a change of the droplet size as ejected.

Preferably, a selective, patterned hard amorphous carbon film, e.g. diamond like carbon (DLC), of for example 400 nm ($10^{-9}$ m) is deposited in various areas, notably inside all or part of cavity 7 and output channel 10, certain areas of space 2 and on all or part of the outside of top substrate 5. Such coating further improves smoothness and lowers flow resistance in channel 10. This DLC coating may be applied on the entire exterior surface of top substrate 5, but of course needs to be removed, or not deposited, at those places where the top and bottom substrates are attached to each other by anodic bonding.

Hydrophilic and hydrophobic coatings may be applied selectively on top substrate 5 and on bottom substrate 6 as required by the flow characteristics of the medication or liquid substance 3.

The ratios between the different individual dimensions, such as the internal volume height of space 2, the distance between the nozzles 9, the length of the membrane part of bottom substrate 6 etc. result in factors such as compression ratio, stroke amplitude of the membrane etc. which together with the electronic parameters such as amplitude and frequency allow to adapt the inventive spray device to various liquid characteristics such as viscosity.

Thanks to the inventive arrangement of spray device 1, virtually mono-dispersive droplets are ejected which allow for a precise calculation of the amount of drug which will enter the various parts of the lungs.

Figure 5A:
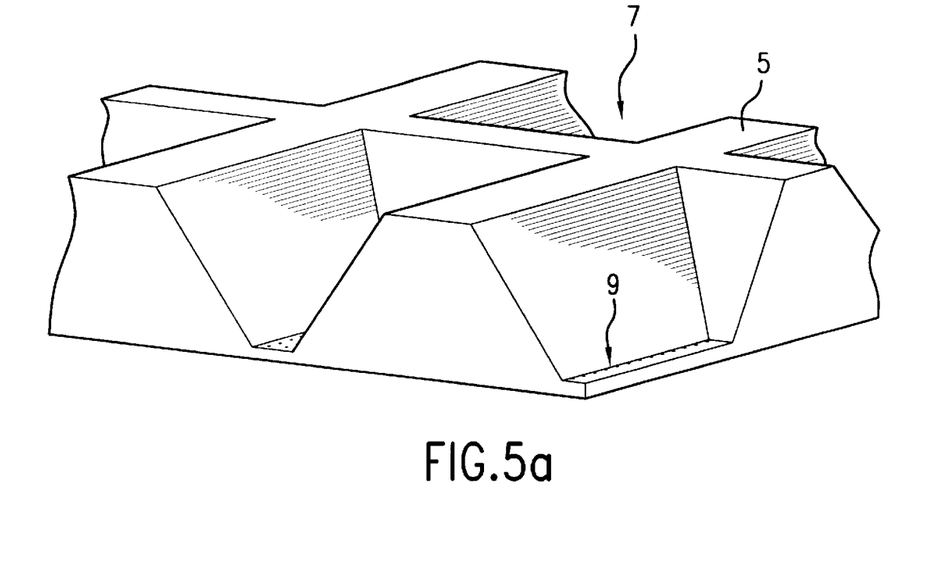
FIG. 5 shows a schematic detailed view of a top substrate of the liquid droplet spray device according to the present invention.
Figure 5B:
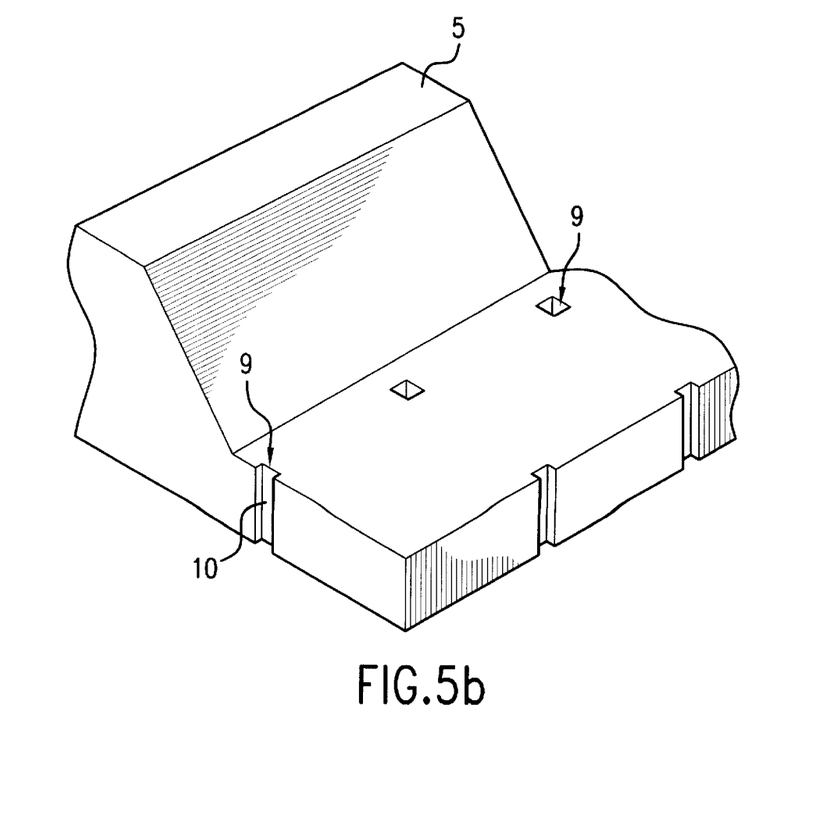

FIG. 5a shows a detailed view of top substrate 5 comprising cavities 7, outlet channels 10 and outlet nozzles 9. As the top surface of cavity 7 forming the aforementioned membrane is much larger than the actual nozzle surface, it is thus possible to provide several outlet nozzles 9 on each cavity surface in order to eject more droplets simultaneously, and thus a larger amount of drug. FIG. 5b shows a close-up view of a part of FIG. 4a in which it can be seen that the channels 10 and nozzles 9 may be readily placed according to the specific conditions.

Advantageously, several cavities 7 can also be combined to form a single elongated cut-off pyramid-shaped trench, and even several of these trenches may be combined in a suitable arrangement. An increased internal volume is then obtained which also has a lower impact risk for the excited liquid trying to leave the device. Furthermore, such an arrangement is easier to manufacture and is thus lower in cost.

The diameter of a droplet depends on the nozzle hole size for a given frequency of the vibration of the liquid substance and the inlet pressure. In the present example where a frequency of around 243 kHz is used, the droplet diameter has been found to be around 5 $\mu$m, the diameter of the hole of nozzle 9 is around 7 $\mu$m and the inlet pressure is a few millibar. One such a droplet thus contains a quantity of around 67 femtoliters ($10^{-15}$l) so that as such the number of nozzles may be determined as a function of the amount to be ejected. In a practical case, the number of nozzles may vary from around 600 to about 1500.

In a preferred embodiment, a medication flow measurement device or means, such as, e.g., a piezoresistive element, referenced by reference numeral 16, see FIG. 1, is provided on the inner surface of the membrane near the outlet nozzles by way of a differential pressure sensor allowing a more complete supervision of the spray device by not only measuring the flow, but which may also detect an empty space 2 as well as a possible occlusion. The amount of droplets to be ejected may be controlled by the medication flow measurement device within the spray device so as to allow for a determination of the amount ejected.

The piezoresistive flow measurement device 16, which may be deposited or diffused into the inner membrane of top substrate 5, can also be calibrated to measure temperature. It can thus be interfaced the electronic device or means 100 for the purpose of flow measurement as well as temperature measurement, thus serving as an input to said electronic device 100 for the calculation of correct operating modes under varying ambiental conditions of the aforementioned heating and of correction factors for compensation of its own non-linearities and those of vibrating means 8 and liquid droplet spray device 1.

The present Applicant has further used, and implemented in electronic circuitry, a model of the lungs and of their functioning. Details of this lung model are described in European patent application no. 98111497.8 and of the electronic control circuit, which is a rule processor, in European patent EP-B-0 748 482. Indeed, it has been observed that a certain droplet size is more suitable for effectively reaching the different regions. For example, a droplet having a size of around 3 to 5 $\mu$m will easier reach the alveoli region, but a droplet with a size of around 10 $\mu$m will reach the centre region, whereas a droplet size of around 16 $\mu$m assures that the droplets arrive at the trachea region.

Thanks to these observations, it is thus possible to determine which droplet size and dosage of a drug is to be used for a desired therapy and for a type of patient (infant, child or adult) and to design the inhaler according to the required dosage.

Having described a preferred embodiment of this invention, it will now be apparent to one of skill in the art that other embodiments incorporating its concept may be used. It is felt, therefore, that this invention should not be limited to the disclosed embodiment, but rather should be limited only by the scope of the appended claims.

What is claimed is:

1. A liquid droplet spray device for atomizing an inhaled liquid substance, comprising:

a housing formed of a superposition of a first substrate and a second substrate;

a space within the housing and enclosed by said first and second substrates for containing the liquid substance;

a supply device connected to supply said liquid substance to said space;

a vibrating device disposed to apply a frequency of vibration to said liquid substance thereby generating said liquid droplet spray; and an outlet arrangement disposed to eject said liquid droplet spray when said liquid substance undergoes said vibration, said outlet arrangement comprising at least one cavity arranged in one of said substrates and forming part of said space of said housing;

wherein said outlet arrangement is located in said first substrate and said vibrating device is arranged on said second substrate, said outlet arrangement further comprising one or more output nozzles and at least one output channel connecting said cavity to said output nozzles, and wherein said outlet arrangement is disposed such that output nozzles are superposed on vibration mode peaks of a standing wave pattern creatable in said space.

2. A liquid droplet spray device according to claim 1, wherein said supply device supplies said liquid substance at a low input pressure which has a constant and repeatable level for a plurality of atomization cycles.

3. A liquid droplet spray device according to claim 1, wherein said output nozzle and said output channel have a non-tapered shape of tightly toleranced vertical length and diameter.

4. A liquid droplet spray device according to claim 1, wherein said outlet device is adaptable to a certain type of medication, wherein the dimensions of said substrate and said space are adaptable for providing optimum shape of said space and compression ratio of liquid in said space adapted for a certain type of medication.

5. A liquid droplet spray device according to claim 1, wherein said space and said outlet arrangement are delimited by areas which are covered with a hydrophilic coating and/or areas covered with a hydrophobic coating.

6. A liquid droplet spray device according to claim 5, wherein said hydrophobic coating is a diamond-like carbon.

7. A liquid droplet spray device according to claim 6, wherein said first and second substrates are joined by anodic bonding.

8. A liquid droplet spray device according to claim 1, wherein said vibrating device includes a piezoelectric element, a piezoresistive element in contact with said top substrate and an electronic means for detecting a particular vibration mode of said piezoelectric element, for maintaining that particular mode and for compensating for non-linear effects due to a change in ambient conditions of said spray device.

9. A liquid droplet spray device according to claim 8, wherein said vibrating device and said electronic means are arranged to provide a particular vibration mode for reversal of the flow direction, thereby completely emptying, or drying said space so as to obtain a minimal retention and for maintaining that particular mode and for compensating for any non-linear effects due to a change in ambient conditions of said spray device.

10. A liquid droplet spray device according to claim 1, wherein said spray device further comprises a heater disposed to heat said liquid substance.

11. A liquid droplet spray device according to claim 10, wherein said heater comprises operating said vibrating device at a particular frequency of vibration and mode so as to provoke such heating.

12. A liquid droplet spray device according to any one of claims 1 to 11, wherein said second substrate has a geometrical shape similar to that of said first substrate, but only one of said substrates having said at least one output nozzle.

13. A liquid droplet spray device according to any one of the claims 1 to 11, wherein said second substrate has a geometrical shape and is made of a material which are similar to that of said first substrate, but only one of said substrates has said at least one output nozzle.

14. A liquid droplet spray device according to claim 1, wherein said second substrate also comprises said outlet arrangement, but without said one or more output nozzles.

15. A liquid droplet spray device according to claim 1, wherein said outlet device is adaptable to a certain type of liquid, wherein the dimensions of said substrate and said space are adaptable for providing optimum shape of said space and compression ratio of liquid in said space adapted for the certain type of liquid.

16. A liquid droplet spray device according to claim 1, wherein said one or more output nozzles comprise a plurality of nozzles.

17. A liquid droplet spray device according to claim 1, wherein said one or more output nozzles comprise a plurality of nozzles, and each nozzle is contiguous with a corresponding output channel that is contiguous with a corresponding cavity.

18. A method of dispensing an inhalable atomized liquid with a liquid droplet spray device comprising:

a housing formed of a superposition of a first substrate and a second substrate;

a space within the housing and enclosed by said first and second substrates for containing the liquid substance;

a supply device connected to supply said liquid substance to said space;

a vibrating device disposed to apply a frequency of vibration to said liquid substance thereby generating said liquid droplet spray; and an outlet arrangement disposed to eject said liquid droplet spray when said liquid substance undergoes said vibration, said outlet arrangement comprising at least one cavity arranged in one of said substrates and forming part of said space of said housing;

wherein said outlet is located in said first substrate and said vibrating device is arranged on said second substrate, said outlet arrangement further comprising one or more output nozzles and at least one output channel connecting said cavity to said output nozzles;

said method comprising the steps of:

(a) supplying said liquid substance to said space;

(b) creating a standing wave pattern within said space, such that said nozzles are superposed on vibration mode peaks of said standing wave pattern; and (c) applying a frequency of vibration to said liquid substance sufficient to generate said liquid droplet spray, and eject said spray from said output nozzle.

19. A method according to claim 18, wherein said step of supplying said liquid substance is carried out at a low input pressure at a constant and repeatable level for a plurality of atomization cycles.

20. A method according to claim 18, further comprising the step of adapting said outlet arrangement to a certain type of liquid to be atomized, wherein the dimensions of said substrate and said space are adapted for providing optimum shape and compression suitable for ejecting said liquid.

21. A method according to claim 18, comprising providing areas delimiting said outlet or said space which are covered with hydrophilic and/or hydrophobic coatings.

22. A method according to claim 18, further comprising:
providing a piezoelectric element included in said vibrating device;
providing a piezoresistive element in contact with or part of said top substrate;
detecting a particular vibration mode of said piezoelectric element;
maintaining a desired vibration mode based on said detected mode; and
compensating for non-linear effects due to a change in ambient conditions.

23. A method according to claim 22, further comprising creating a particular vibration mode for reversal of a flow direction of liquid, thereby completely emptying, or drying said space.

24. A method according to claim 18, further comprising the step of heating said liquid substance.

25. A method according to claim 24, wherein said step of heating is provided by operating said vibrating device at a particular frequency of vibration and mode so as to provoke such heating.

26. A method according to claim 18, wherein said one or more output nozzles comprise a plurality of nozzles so that said spray is ejected from said plurality of nozzles.

27. A method of generating an atomized spray for inhalation comprising the steps of:
providing a space having one or more output nozzles;
supplying liquid to said space at a low pressure;
creating a standing wave pattern within said space, such that the output nozzles are superposed on vibration mode peaks of said standing wave pattern; and
applying a frequency of vibration to said liquid sufficient to generate said atomized spray and eject said spray through the output nozzle.

28. A method according to claim 27, wherein said steps of creating a standing wave pattern and applying a frequency of vibration are carried out by a piezoelectric element.

29. A method according to claim 27, further comprising the steps of: detecting a particular vibration mode of said piezoelectric element; maintaining a desired vibration mode based on said detected mode; and compensating for non-linear effects due to a change in ambient conditions.

* * * * *